United States Patent [19]
Chen et al.

[11] Patent Number: 6,133,197
[45] Date of Patent: *Oct. 17, 2000

[54] MICROENCAPSULATED COMPOSITIONS

[75] Inventors: Jin-Ling Chen, El Cerrito; Marius Rodson, El Sobrante; Herbert B. Scher, Moraga; Kuo-Shin Lee, deceased, late of El Cerrito, all of Calif., by Chi Chang Lee, administrator

[73] Assignee: ZENECA Limited, United Kingdom

[*] Notice: This patent issued on a continued prosecution application filed under 37 CFR 1.53(d), and is subject to the twenty year patent term provisions of 35 U.S.C. 154(a)(2).

[21] Appl. No.: 08/861,211

[22] Filed: May 21, 1997

Related U.S. Application Data

[60] Provisional application No. 60/018,220, May 23, 1996.
[51] Int. Cl.$^7$ ............................. A01N 3/02; A01N 59/24; A01N 57/00; A01N 43/40
[52] U.S. Cl. ...................... 504/116; 504/189; 504/206; 504/245; 504/256; 504/258; 71/11; 71/28; 71/64.07; 71/64.11; 71/903
[58] Field of Search .................. 71/11, 28, 64.07, 71/64.11, 903; 504/116, 189, 245, 256, 258, 206

[56] References Cited

U.S. PATENT DOCUMENTS

| | | | |
|---|---|---|---|
| 3,656,997 | 4/1972 | Cordes | 424/456 |
| 4,056,610 | 11/1977 | Barber et al. | 424/32 |
| 4,140,516 | 2/1979 | Scher | 71/88 |
| 4,235,872 | 11/1980 | Tocker | 424/19 |
| 4,285,720 | 8/1981 | Scher | 71/88 |
| 4,448,929 | 5/1984 | Rodson et al. | 525/57 |
| 4,497,793 | 2/1985 | Simkin | 424/32 |
| 4,557,755 | 12/1985 | Takahashi et al. | 71/100 |
| 5,073,191 | 12/1991 | Misselbrook et al. | 71/121 |
| 5,229,122 | 7/1993 | Chadwick et al. | 424/408 |
| 5,262,173 | 11/1993 | Sheth et al. | 424/494 |
| 5,310,721 | 5/1994 | Lo | 504/116 |

*Primary Examiner*—Jose' G. Dees
*Assistant Examiner*—Alton Pryor
*Attorney, Agent, or Firm*—David P. LeCroy

[57] ABSTRACT

Polyurea microcapsules particularly suitable for foliar application are prepared by an interfacial polymerization process in which the polyurea is formed from an aromatic diisocyanate and optionally an aromatic polyisocyanate having 3 or more isocyanate groups, in a weight ratio (when both types of isocyanate are present) of polyisocyanate:diisocyanate of from about 1:100 to about 1:1.5, and in which the microcapsules are produced having an average particle size of from about 1 to about 5 microns.

As compared to conventional liquid (e.g., emulsifiable concentrate) compositions of pesticides, the microcapsules can provide safer handling and higher loading of active ingredients, while providing substantially equivalent biological activity to the liquid compositions.

13 Claims, 5 Drawing Sheets

Figure 3 Control of Artifical Infested Neonate *Heliothis Virescens* in Cotton at o day Figure 4 Control of Artifical Infested Neonate *Heliothis Virescens* in Cotton at 1 day Figure 5. Fluazifop-p-butyl Microcapsules

MICROENCAPSULATED COMPOSITIONS

This application claims the benefit of provisional application No. 60/018,220 filed May 23, 1996.

This invention relates to certain microencapsulated compositions, particularly pesticide compositions, particularly such compositions as are useful for application to established plants, i.e., by foliar application.

Microencapsulation of pesticides and other agricultural chemicals has been performed for a number of years, using various microencapsulation processes or techniques, and in connection with a number of different active ingredients. In general, the object of producing such compositions has been to provide controlled release of the active ingredient, and particularly to provide a release for longer term efficacy so that it is released over a period of time and is available throughout the effective period. This is particularly significant for pesticides or other ingredients which are degraded or decomposed over a relatively short period of time or under certain environmental conditions. Use of a microencapsulated composition provides effective activity of the active ingredient over a longer period of time since it will be released continuously into the environment rather than in one initial dose (as would be the case with nonencapsulated or non-controlled release formulations such as solutions, emulsions, granules, etc.).

Microencapsulated pesticides are used primarily as preemergence pesticides, that is, they are applied to soil prior to the emergence of vegetation or appearance of insects so that they are available to kill or control newly-emerged weed species or insects in the larval stages. In such applications, relatively slow release rates are desired so that the pesticide is released into the environment over a period of time, usually over at least several weeks.

In general, microencapsulated forms of agrochemicals are produced by one of three general methods: physical methods, phase separation methods and interfacial polymerization. In the third of these methods, namely interfacial polymerization, the microcapsule walls are formed of polymeric material produced by a polymerization reaction which preferably takes place at the interface between two phases, usually an aqueous phase and a water-immiscible organic phase. Usually the two phases are in the form of an oil-in-water emulsion; alternatively they may be in the form of a water-in-oil emulsion.

U.S. Pat. No. 4,285,720 discloses a process for production of microencapsulated water-immiscible material, including pesticides and other agrochemicals, by interfacial polymerization techniques. In general, the process involves production of an aqueous phase containing water, one or more surfactants, and a protective colloid and an organic phase which comprises the material to be encapsulated, optionally one or more solvents, and one or more organic polyisocyanates. Either the material to be encapsulated or the solvent may also serve as a solvent for the polyisocyanates.

The two phases are then mixed so as to produce a physical dispersion of the organic phase in the aqueous phase. This is usually done by adding the organic phase to the aqueous phase with stirring. The stirring and other conditions are adjusted to produce an oil-in-water emulsion where the organic phase (in the form of droplets of a desired size) is dispersed in the aqueous phase. Then, by adjusting the pH of the resulting mixture and the temperature, a condensation reaction of the polyisocyanate is effected at the interfaces between the organic phase droplets and the aqueous phase, forming the polymer or shell wall of the microcapsules, enclosing the organic phase.

The process as described in U.S. Pat. No. 4,285,720 contemplates utilizing one or more polyisocyanates, and can produce microcapsules having a droplet size of from about 0.5 to about 4,000 microns, preferably from about 1 to about 100 microns. The microcapsules produced in accordance with the examples of this patent, and following its general teachings, have proven to be very effective in providing controlled and relatively long-term release (over weeks) of various pesticides.

However, different properties are required of microencapsulated materials to be used for foliar application. As opposed to relatively long-term, controlled release, microcapsules for foliar application require relatively quick release of all the material to provide rapid pesticidal activity.

Notable among pesticides utilized for protection of plants against insects are the pyrethroids. In current agricultural practice, compositions containing pyrethroids for application to plant foliage are provided in nonencapsulated forms, typically as emulsifiable concentrates and wettable powders, which are mixed with water to form compositions which are then sprayed on the plants.

Handling of pyrethroids, however, is known in some cases to provoke an adverse skin reaction. This reaction has been described as a burning, tingling, numbing or prickling sensation, which is most pronounced on regions of the handler's face. This reaction, known as paraesthesia, is generally associated with trace amounts of the pyrethroid being transferred to the handler's face through inadvertent touching by a contaminated hand. The problem can be particularly acute in solid formulations such as dusts and granules.

Microencapsulation of pesticides may often provide an increase in the safety of pesticide handling, to the extent that the polymer wall of a microcapsule minimizes contact of the handler with the active pesticide. Microencapsulation of a pesticide may also afford advantages such as the possibility of providing the material in a relatively more concentrated form than a corresponding emulsifiable concentrate, wettable powder or dust, correspondingly reducing the amount of inert materials such as solvents, surfactants, dispersants, supports, etc., which are employed and released into the environment. However, the typical slow controlled release microcapsules which have up to now been utilized for soil application of pesticides are not satisfactory for application where a relatively quick and complete release is needed.

SUMMARY OF THE INVENTION

This invention comprises a process for preparing microcapsules comprising the steps of (a) preparing an organic phase comprising a water-immiscible material to be encapsulated, an aromatic diisocyanate and optionally an aromatic polyisocyanate containing 3 or more isocyanate groups, in which the weight ratio of aromatic polyisocyanate to aromatic diisocyanate is up to about 1:1.5; (b) introducing the organic phase into an aqueous phase comprising water, a protective colloid, and optionally a surfactant; (c) mixing under high shear to form an oil-in-water emulsion in which the oil droplets have an average size of from about 1 to about 5 microns; and (d) adjusting as necessary the temperature and/or pH of the oil-in-water emulsion such that an interfacial polymerization reaction occurs forming polyurea microcapsules containing the organic phase.

DETAILED DESCRIPTION OF THE DRAWINGS

DETAILED DESCRIPTION OF THE INVENTION

It has been found that microencapsulated agricultural chemicals having a relatively quick release and suitable for foliar application can be prepared utilizing the general process described in U.S. Pat. No. 4,285,720 with two essential changes and modifications. These relate to the use of a monomer or mixture of monomers as described herein which produces microcapsules having no or relatively low cross-linking in the walls, and the formation of an oil-in-water emulsion in which the oil phase comprises relatively small droplets having an average particle size of from about 1 to about 5 microns, preferably from about 2 to about 4.5 microns. In addition, because of the relatively small size the capsules of this invention are produced having relatively thin walls. The contents of U.S. Pat. No. 4,285,720 are hereby incorporated by reference herein.

In brief, the process involves encapsulation of a water immiscible material (in the present case preferably an organic phase containing a pyrethroid insecticide) within discrete capsules of polyurea. In this process, hydrolysis of an isocyanate monomer to form an amine occurs, and that in turn reacts with another isocyanate monomer to form the polyurea. In general, the process comprises two stages.

In the first stage, a physical dispersion of a water-immiscible phase in an aqueous phase is prepared. The water-immiscible phase comprises the pesticide to be encapsulated together with other material as described below. As is known in the art, the dispersion is produced by a high shear device, and this step is carried out until the desired droplet size (as discussed below) is obtained. Only mild agitation is required for the remainder of the process.

In the second stage, the dispersion is stirred under high shear and maintained at a temperature range of from about 20° C. to about 90° C., during which reaction occurs involving the organic diisocyanate and organic polyisocyanate to form the polyurea at the interfaces between the droplets of the organic phase and the aqueous phase. Adjustment of the pH of the resulting mixture and the temperature range during the second stage advance this condensation reaction.

The aqueous phase is prepared from water, a protective colloid, and preferably a surfactant. In general, the surfactant or surfactants in this phase may be anionic or nonionic surfactants with an HLB range of from about 12 to about 16. If more than one surfactant is used, individual surfactants may have HLB values lower than 12 or higher than 16 as long as the overall HLB value of the combined surfactants will be within the range of about 12–16. Suitable surfactants include polyethylene glycol ethers of linear alcohols, ethoxylated nonylphenols, naphthalene sulfonates, salts of long chain alkyl benzene sulfonates, block copolymers of propylene and ethylene oxides, anionic/nonionic blends, and the like. Preferably the hydrophobic portion of the surfactant has chemical characteristics similar to the water-immiscible phase. Thus, when the latter contains an aromatic solvent, one suitable surfactant would be an ethoxylated nonylphenol. Particularly preferred surfactants include block copolymers of propylene oxide and ethylene oxide, and anionic/nonionic blends.

The protective colloid present in the aqueous (or continuous) phase must absorb strongly onto the surface of the oil droplets and can be selected from a wide range of such materials including polyacrylates, methyl cellulose, polyvinyl alcohol, polyacrylamide, poly (methylvinyl ether/maleic anhydride), graft copolymers of polyvinyl alcohol and methylvinyl ether/maleic acid [hydrolyzed methylvinyl ether/maleic anhydride (see U.S. Pat. No. 4,448,929, which is hereby incorporated by reference herein)]; and alkali metal or alkaline earth metal lignosulfonates. Preferably, however, the protective colloid is selected from alkali metal and alkaline earth metal lignosulfonates, most preferably sodium lignosulfonates.

The range of surfactant concentration (when a surfactant is used) in the process is from about 0.01 to about 3.0 percent by weight, based on the aqueous phase, but higher concentrations of surfactant may also be used. The protective colloid is generally present in the aqueous phase in an amount of from about 0.1 to about 5.0 percent by weight. The amount of protective colloid employed will depend on various factors, such as molecular weight, compatibility, etc., so long as enough is present to completely coat the surfaces of all the oil droplets. The protective colloid can be added to the aqueous phase prior to the addition of the organic phase, or can be added to the overall system after the addition of the organic phase or the dispersion of it. The surfactants should be chosen so as to not displace the protective colloid from the droplet surfaces.

The organic phase comprises a water immiscible pesticide and/or other agricultural chemical to be encapsulated, optionally one or more solvents, an aromatic diisocyanate and preferably also an aromatic polyisocyanate. Suitable solvents include aromatic hydrocarbons such as xylenes, naphthalenes, or mixtures of aromatics; aliphatic or cycloaliphatic hydrocarbons such as hexane, heptane and cyclohexane; alkyl esters including alkyl acetates and alkyl phthalates, ketones such as cyclohexanone or acetophenone, chlorinated hydrocarbons, vegetable oils, or mixtures of two or more such solvents.

We have now found that by modifying the process of U.S. Pat. No. 4,285,720, microcapsules which provide a relatively quick release of the encapsulated contents when applied in an agricultural environment can be obtained.

The quick release feature is accomplished by providing microcapsules having no, or relatively little, cross-linkage in the polymeric walls, and having a relatively small average particle size (as discussed below). The walls are formed either only of aromatic diisocyanate or a mixture of one or more aromatic diisocyanates with an aromatic polyisocyanate having 3 or more isocyanate groups in which the weight ratio of polyisocyanate to diisocyanate is from about 1:100 to about 1:1.5, preferably from about 1:50 to about 1:10.

The diisocyanate and the polyisocyanates which may be used in this invention are those described in U.S. Pat. No. 4,285,720. Diisocyanates usable in the process of this invention include m-phenylene diisocyanate, p-phenylene diisocyanate; 1-chloro-2,4-phenylene diisocyanate; 4,4'-methylenebis (phenyl isocyanate); 3,3'-dimethyl-4,4'-biphenylene diisocyanate; 4,4'-methylenebis (2-methylphenyl isocyanate); 3,3'dimethoxy-4,4'-biphenylene diisocyanate; 2,4tolylene diisocyanate; 2,6-tolylene diisocyanate, isomeric mixtures of 2,4- and 2,6-tolylene diisocyanate and 2,2',5,5'-tetramethyl4,4'-biphenylene diisocyanate.

Aromatic polyisocyanates usable in this invention have 3 or more isocyanate groups and include polymethylene polyphenylisocyanate (available from ICI or Bayer), triphenylmethane triisocyanate ("Desmodur R") and the adduct formed between 1 mole of trimethylolpropane and 3 moles of tolylene diisocyanate ("Desmodur TH") (Desmodur products available from Bayer A.G.).

Whether a polyisocyanate is needed, and if so the relative amount, to provide the necessary wall properties, will depend on the active ingredient or ingredients in the composition, and the use to which the composition will be put. For instance, we have found that for microencapsulated compositions containing the herbicide fluazifop-P-butyl for foliar application, satisfactory capsules can be prepared using only mixed isomers of tolylene diisocyanate without a polyisocyanate, and that in mixtures the weight ratio of polyisocyanate to diisocyanate may be as high as about 1:1.5. However, for compositions containing the insecticide lambda-cyhalothrin, some polyisocyanate is required to produce cross-linking in the capsule walls. There the weight ratio of polyisocyanate:diisocyanate should be from about 1:100 to about 1:3, preferably from about 1:50 to about 1:10.

While U.S. Pat. No. 4,285,720 discloses the uses of mixtures of these two types of isocyanates, specifically tolylene diisocyanate (TDI) (various isomers) and polymethylene polyphenylisocyanate (PPI), and the examples demonstrate the use of mixtures of these two isocyanates having a weight ratio of PPI:TDI of from about 2:1 to about 1:1, no other information is provided in this patent on the use of such mixtures.

The total amount of organic isocyanates used in the process will determine the wall content of the microcapsules formed. In general, the isocyanates (and correspondingly the microcapsule walls formed from them) will comprise from about 2.0 to about 15 percent by weight of the microcapsule, most preferably from about 5 to about 10 percent by weight.

The material which is encapsulated is an agricultural chemical, preferably a pesticide, and preferably a material suitable for foliar application. Pesticides for which this invention is applicable include insecticides (particularly pyrethroids), herbicides and fungicides. Other agrochemicals such as plant and insect growth regulators may alternatively be included. The encapsulated material may be a combination of two or more such ingredients.

The second significant change in the process of U.S. Pat. No. 4,285,720 lies in the size of the microcapsules produced, which corresponds to the droplet size of the organic phase in the oil-in-water emulsion. The patent discloses that the desired droplet size was in the range of about 0.5 to about 4,000 microns, with the preferred range for most pesticidal applications being from about 1 to about 100 microns. However, in conducting the process according to the present invention, the average particle size should be smaller, namely, from about 1 to about 5 microns, preferably from about 2 to about 4.5 microns. The droplet size can be adjusted by the stirring speed and time, and by the type and amount of surfactant employed, as generally known in the art.

To obtain the appropriate emulsion, the organic phase is added to the aqueous phase with stirring. A suitable dispersing means is employed to disperse the organic phase in the aqueous phase. This means may be any high shear device, operated so as to obtain the desired droplet (and corresponding microcapsule particle) size within the range of about 1 to about 5, preferably about 2 to about 4.5 microns. Once the proper droplet size is obtained, the dispersion means is discontinued and only mild agitation is required for the remainder of the process.

To form the microcapsules, the temperature of the two-phase mixture is then raised from ambient to a value of from about 20° C. to about 90° C., preferably about 40° C. to about 90° C. Depending on the system, as described in U.S. Pat. No. 4,285,720, the pH value may be adjusted to an appropriate level.

In addition to the liquid pesticide or other agricultural chemical, the organic phase may also contain a suspended biologically active solid, as described in PCT Application No. 95/13698; for example, it may contain a second solid pesticide suspended in a liquid pesticide. Alternatively, if an encapsulated pesticide is sensitive to and subject to degradation by ultraviolet or actinic light, the microcapsules may also contain a suspended solid ultraviolet light protectant selected from titanium dioxide, zinc oxide and mixtures of titanium dioxide and zinc oxide, as described in our co-pending patent application entitled "Microcapsules Containing Suspensions of Biologically Active Compounds and Ultraviolet Protectant", Serial No. 08/430,030 filed Apr. 27, 1995.

Utilization of the improvement of this invention results in the production of microencapsulated pesticides which have the safety advantages of microcapsules during handling, and which perform equivalently to liquid formulations such as emulsifiable concentrates of these pesticides when applied. Additionally, the use of the microcapsules of this invention permits substituting for the previously used emulsifiable concentrates an equally effective microencapsulated formulation which may contain a higher concentration of the pesticide and correspondingly lower concentrations of solvents, surfactants and the like, thus reducing the amounts of the latter released into the environment. This latter improvement is possible because microcapsules can be prepared having highly saturated solutions or suspensions of pesticides in organic solvents whereas the same concentrations might not be suitable for use in emulsifiable concentrates, because of a potential that the pesticide may crystallize out of the composition during storage, handling, and other situations. Additionally, the microcapsules are produced in a water-based formulation, i.e., as an aqueous suspension of the capsules, which further reduces the relative amount of solvent in the formulation, and consequently introduced into the environment, as compared to an emmulsifiable concentrate.

Capsules of this invention have been shown to provide bioactivity approximately equal to that of an emulsifiable concentrate. They therefore are suitable for use in place of emulsifiable concentrates in general—not only for foliar application to plants, but for other applications as well, such as to soil or in or around buildings.

The invention is illustrated by the following examples:

The general procedure for preparation of the microencapsulated lambda-cyhalothrin products was as follows:

The organic phase was prepared by dissolving technical grade (88% purity) lambda-cyhalothrin in the solvent. If titanium dioxide was included, as in Example 3, dispersants were first added to the solution, followed by the titanium dioxide. Finally the organic isocyanates were added.

The aqueous phase was prepared by dissolving the specified ingredients in water. The organic and aqueous phases were then combined with agitation provided by a high-speed stirrer to form an oil-in-water emulsion. Stirring was continued until the average size of the oil droplets was 3.0±1 micron. Then, while maintaining mild agitation, the temperature of the emulsion was raised to 50° C. over a period of 30 minutes, and maintained at that level for 3 hours, during which the microcapsule shells formed.

The resulting suspension was allowed to cool to room temperature. The additional ingredients were then added to produce a more stable suspension with adjustment of the pH to a value of 5.0 by the sulfuric acid. The capsule size corresponded to the original oil droplet size. Observation under a microscope showed well-formed, discrete particles.

Ingredients used in the following examples were:

lambda-cyhalothrin, technical grade (88% purity)

Solvesso 200 aromatic solvent (available from Exxon)

titanium dioxide—USP328—0.3 micron particle size, from Whittaker, Clark & Daniels Ltd.

Hypermer LP1, Hypermer LP5 and Atlox 4912 dispersants (available from ICI)

Reax 100M protective colloid (sodium salt of lignosulfonic acid, 40% wt. solution in water, available from Westvaco Chemicals)

Tergitol NP7 and XD surfactants (available from Union Carbide)

Witconate 90 surfactant (available from Witco)

Kelzan (xanthan gum, available from Monsanto)

Proxel GXL (biocide, available from ICI)

The amounts of the ingredients are given in the examples.

EXAMPLE 1

| Component | Composition | |
|---|---|---|
| | Weight, g | Weight, % |
| ORGANIC PHASE | | |
| Lambda-cyhalothrin (technical grade) | 116.8 | 29.2 |
| Solvesso 200 | 54.8 | 13.7 |
| Polymethylene Polyphenylisocyanate | 0.4 | 0.1 |
| Toluene Diisocyanate (80% 2,4-isomer; 20% 2,6-isomer) | 13.5 | 3.4 |
| AQUEOUS PHASE | | |
| Reax 100M (40% wt. solution) | 15.9 | 4.0 |
| Tergitol NP7 (20% wt. solution) | 12.7 | 3.2 |
| Water | 181.7 | 45.4 |
| ADDITIONAL INGREDIENTS | | |
| Ammonia (30% wt. aqueous solution) | 2.0 | 0.5 |
| Kelzan | 0.4 | 0.1 |
| Proxel GXL | 0.4 | 0.1 |
| Concentrated Sulfuric Acid | 1.2 | 0.3 |
| TOTAL | 400.0 | 100.0 |

EXAMPLE 2

| Component | Composition | |
|---|---|---|
| | Weight, g | Weight, % |
| ORGANIC PHASE | | |
| Lambda-cyhalothrin (technical grade) | 103.1 | 25.8 |
| Solvesso 200 | 65.6 | 16.4 |
| Polymethylene Polyphenylisocyanate | 0.4 | 0.1 |
| Toluene Diisocyanate (80% 2,4-isomer; 20% 2,6-isomer) | 13.3 | 3.3 |
| AQUEOUS PHASE | | |
| Reax 100M (40% wt. solution) | 10.3 | 2.6 |
| Witconate 90 | 1.0 | 0.3 |
| Tergitol XD | 3.1 | 0.8 |
| Water | 192.4 | 48.1 |
| ADDITIONAL INGREDIENTS | | |
| Ammonia (30% wt. aqueous solution) | 2.0 | 0.5 |
| Kelzan | 0.5 | 0.1 |
| Proxel GXL | 0.4 | 0.1 |
| Reax 85A | 5.8 | 1.5 |
| Concentrated Sulfuric Acid | 1.9 | 0.5 |
| TOTAL | 400.0 | 100.0 |

EXAMPLE 3

| Component | Composition | |
|---|---|---|
| | Weight, g | Weight, % |
| ORGANIC PHASE | | |
| Lambda-cyhalothrin (technical grade) | 113.2 | 28.3 |
| Solvesso 200 | 58.4 | 14.6 |
| Titanium Dioxide | 9.7 | 2.4 |
| Hypermer LP5 | 6.1 | 1.5 |
| Hypermer LP1 | 2.1 | 0.5 |
| Polymethylene Polyphenylisocyanate | 0.5 | 0.1 |
| Toluene Diisocyanate (80% 2,4-isomer; 20% 2,6-isomer) | 14.8 | 3.7 |
| AQUEOUS PHASE | | |
| Reax 100M (40% wt. Solution) | 10.5 | 2.6 |
| Witconate 90 | 1.0 | 0.3 |
| Tergitol XD | 3.1 | 0.8 |
| Water | 176.5 | 44.2 |
| ADDITIONAL INGREDIENTS | | |
| Ammonia (30% wt. aqueous solution) | 2.0 | 0.5 |
| Kelzan | 0.5 | 0.1 |
| Proxel GXL | 0.4 | 0.1 |
| Concentrated Sulfuric Acid | 1.2 | 0.3 |
| TOTAL | 400.0 | 100.0 |

EXAMPLES 4A–4F—FLUAZIFOP-P-BUTYL

The general procedure for preparation of the microcapsules was as follows:

The organic phase was prepared by mixing 148 g of technical grade fluazifop-P-butyl (90.7% purity) with 12.0 g of tolylene diisocyanate (TDI, mixture of 80% 2,4-isomer and 20% 2,6-isomer) and polymethylene polyphenylisocyanate (PPI) as indicated.

The aqueous phase was prepared by dissolving 3.72 g of Reax 100M (40 wt. % aqueous solution) and 3.72 g of Tergitol XD (20 wt. % aqueous solution) in water. The organic phase was poured into the aqueous phase with stirrings, and the stirring was continued until the average size of the oil droplets was between 4.1 and 4.7 microns. Then, while maintaining mild agitation, the temperature of the emulsion was raised to 50° C. and maintained at that level for 3 hours.

The resulting suspension of microcapsules was allowed to cool to room temperature. Table 1 below describes the capsules.

TABLE 1

| Example No. | 4a | 4b | 4c | 4d | 4e | 4f |
|---|---|---|---|---|---|---|
| Fluazifop-P-butyl wt. % | 43.7 | 43.7 | 43.7 | 43.7 | 43.7 | 43.7 |
| PPI:TDI wt. ratio | PPI only | 80:20 | 60:40 | 40:60 | 20:80 | TDI only |
| Particle size, microns | 4.7 | 4.5 | 4.4 | 4.2 | 4.3 | 4.1 |

BIOLOGICAL EFFICACY EVALUATION

In field tests the biological activity of the products of examples 1–3 was compared against that of a standard emulsifiable concentrate (EC) of lambda-cyhalothrin. As will be shown below, in these tests the level of insect control achieved using the products of this invention was comparable to that using the non-encapsulated products, even on the day of application.

CONTROL OF BOLL WEEVIL (*ANTHONOMUS GRANDI*) ON COTTON

Figure 1:
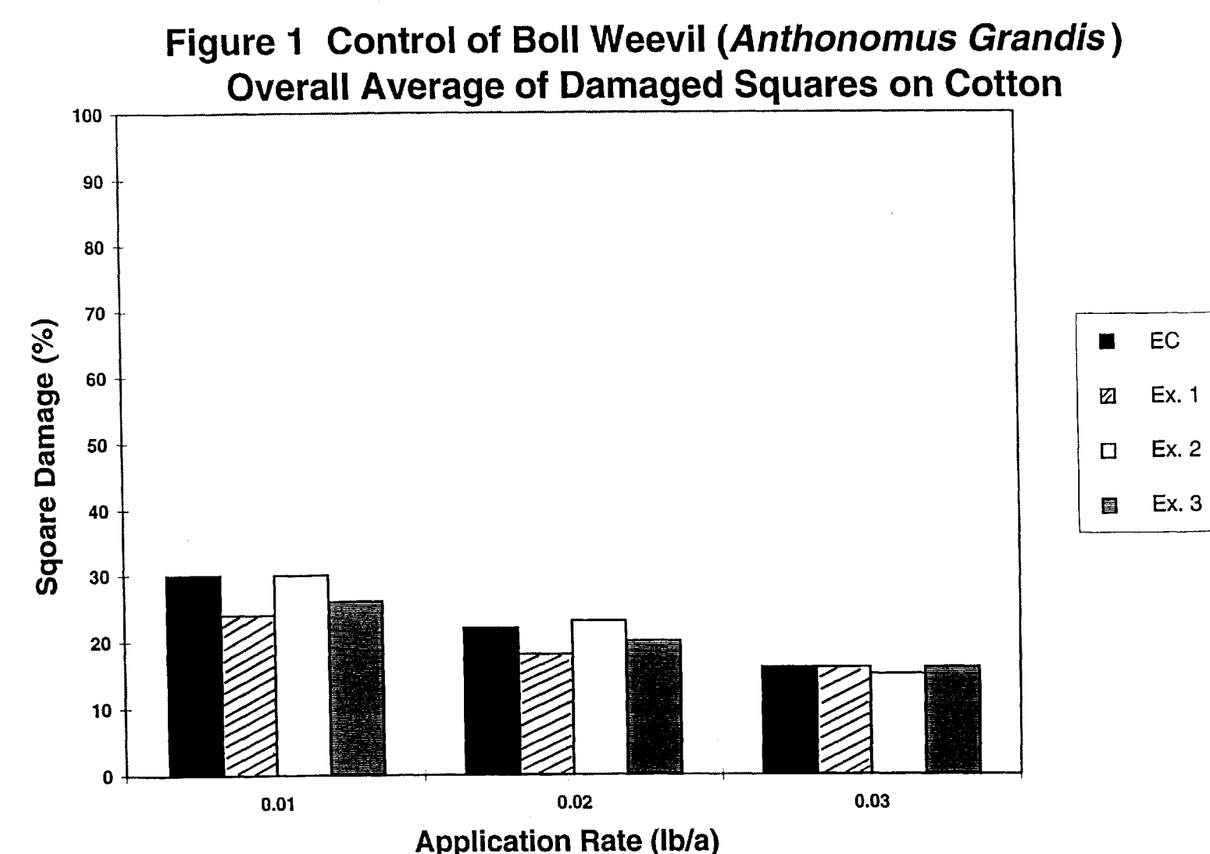
FIGS. 1–5 are graphical depictions of the results of insecticidal and herbicidal evaluations of compositions of this invention.

Products were applied in a randomized complete block, with four replications. Each product was applied at three rates—0.01, 0.02 and 0.03 lb./acre of lambda-cyhalothrin. Activity was evaluated by determining the level of weevil damaged squares (unopened flower buds) (%) in each test plot and this was accomplished by collecting fifty eraser sized squares from each test plot at 3 and 7 days after treatment and evaluating them for weevil damage. Data was subjected to a factorial analysis. The overall results are shown in FIG. 1.

CONTROL OF VELVET BEAN CATERPILLAR (*ANTICARSICA JEMMATALIS*) ON SOYBEAN

Figure 2:
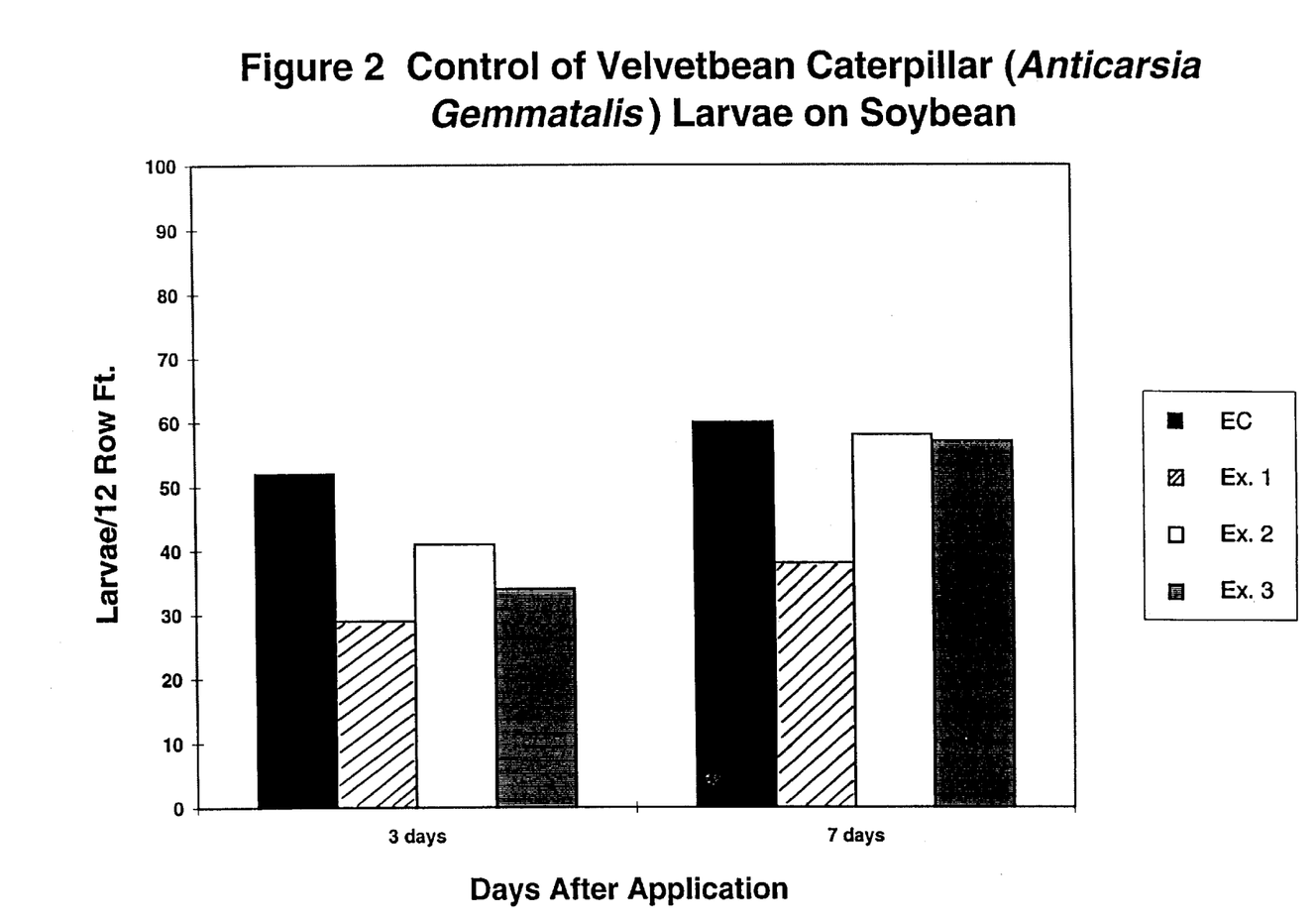

Products were applied in a randomized complete block with four replications. Each formulation was applied at three ratios—0.01, 0.02 and 0.03 lb./acre of lambda-cyhalothrin. Activity was determined by the number of larvae per 12 row feet 3 and 7 days after application. Data was subjected to a factorial analysis. The results are shown in FIG. 2.

CONTROL OF TOBACCO BUDWORM (*HELIOTHIS VIVESCENS*) ON COTTON

Figure 3:
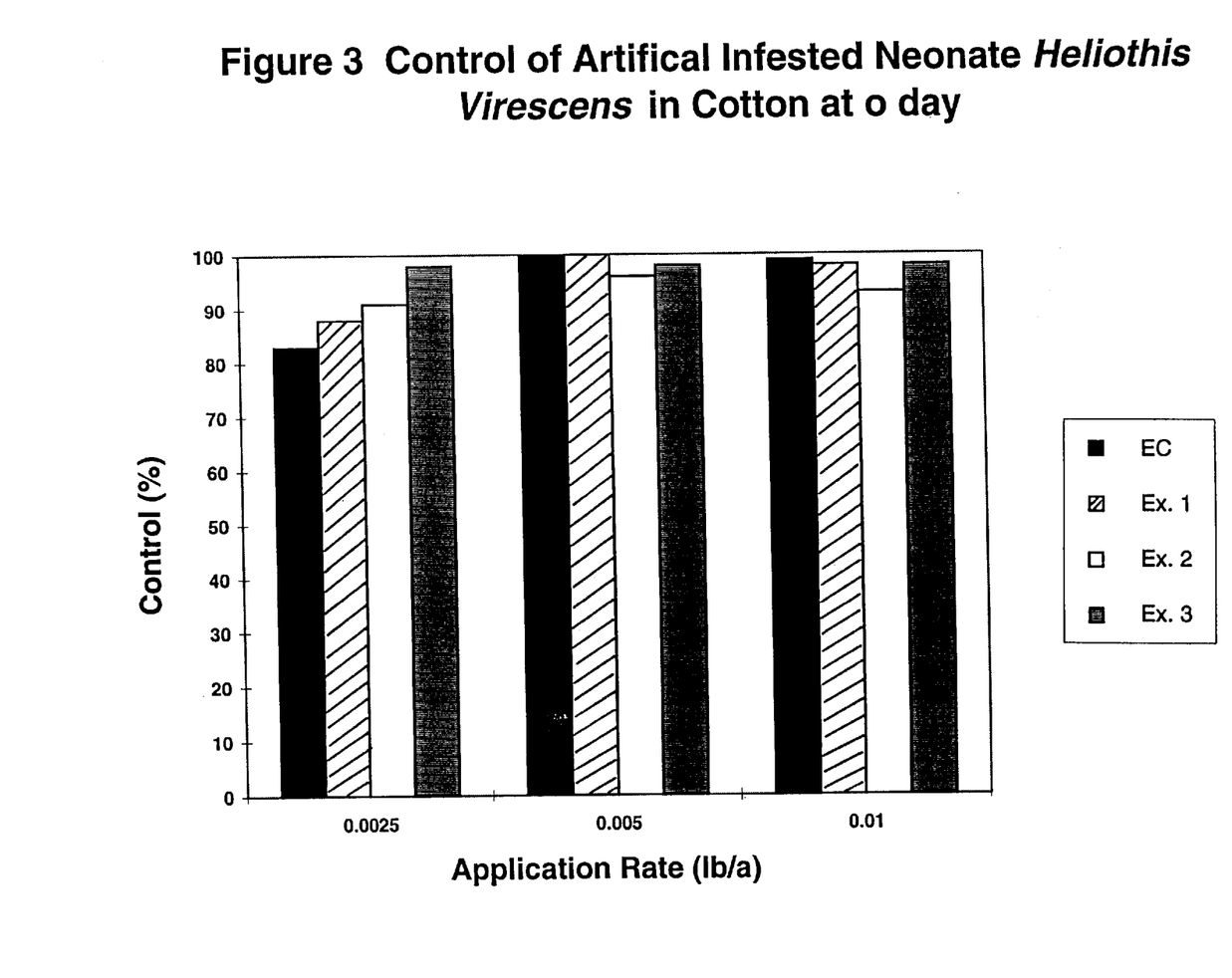
Figure 4:
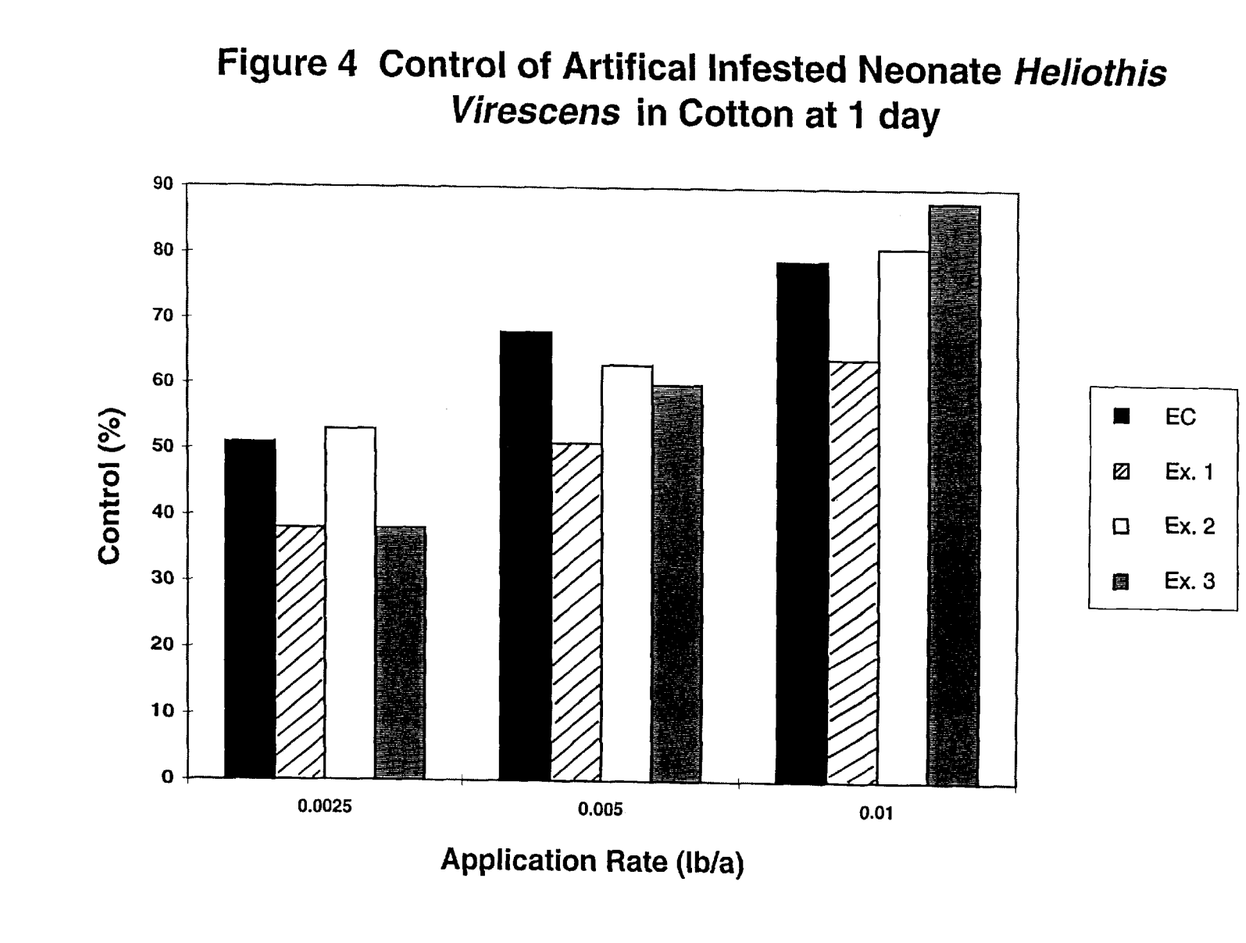

Activity in this test was determined by a laboratory leaf bioassay on field-grown cotton. Each formulation was applied at three rates—0.0025, 0.005 and 0.01 lb./acre lambda-cyhalothrin. Treated leaves were collected in the field, transported to the laboratory and placed in petri dishes together with 1–3 instar budworm larvae (5 larvae per leaf). The results are shown in FIGS. 3 and 4, representing evaluations at 0 and 1 days after treatment, respectively.

In all three tests no statistical difference was shown between formulations applied at comparable rates.

The biological efficacy of the products of examples 4a–4f was compared against that of a standard emulsifiable concentrate (EC) of the herbicide in greenhouse tests.

Sprayable emulsions of the test material were applied post emergence at application rates of 0.016, 0.031, 0.063 and 0.125 lb./acre fluazifop-P-butyl were applied post emergence to flats containing four weed species—green foxtail (*Setaria viridis*), broadleaf signalgrass (*Bracharia platyphylla*), crabgrass (*Digitaria sanguiralis*) and giant foxtail (*Setaria faberi*).

Figure 5:
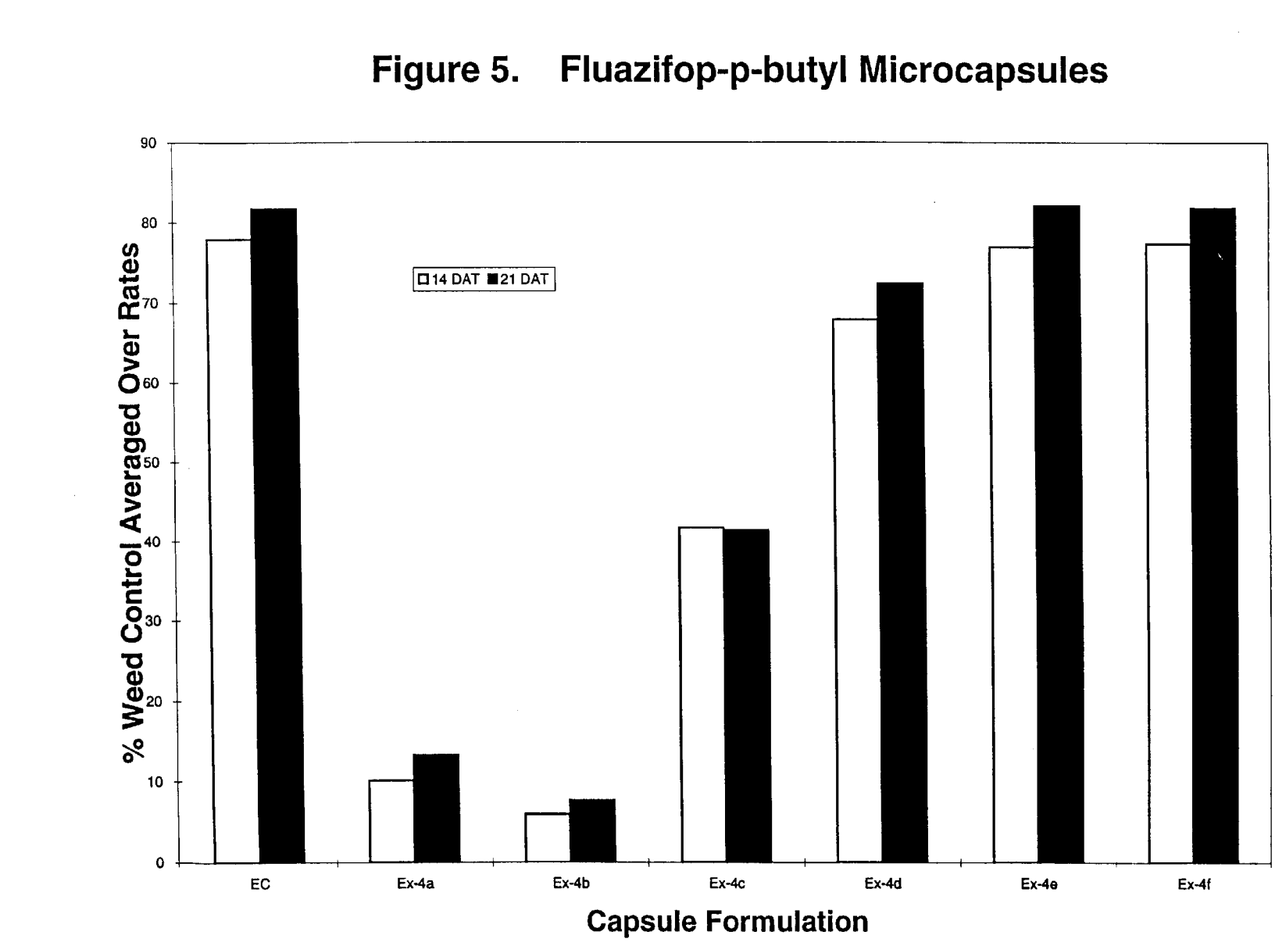

Ratings for weed control were taken at 14 and 21 days after treatment ("DAT"). FIG. 5 shows the ratings of the test materials, averaged over all four rates of application. As can be seen from that figure, compositions prepared using only PPI (Example 4a) or ratios of PPI:TDI greater than 1:1 (Examples 4b and 4c) performed poorly as compared with the emulsifiable concentrate, whereas the compositions of this invention (Examples 4d–4f) showed week control comparable to the EC.

MAMMALIAN TOXICOLOGICAL EVALUATION

Products of Examples 2 and 3 were tested for mammalian skin and eye irritation. For comparison, samples of emulsifiable concentrate ("EC") containing 12.5% by weight lambda-cyhalothrin and a slow-release microencapsulated lambda-cyhalothrin (10 wt. %) ("SR") were included. Test procedures were as follows:

Eye Irritation

Tests were conducted on one group of six New Zealand White rabbits. Body weights were measured on the day of dosing. Weights of all rabbits were in excess of 2 kg. Products were applied at full strength. However, the emulsifiable concentrate at full strength produced parasthesia which prevented a complete assessment in these tests. Therefore, a dilute aqueous spray of the EC (0.5% w/v) was also applied.

Approximately 0.1 ml of each test material was instilled into the conjunctival sac of the left eye of each rabbit and the lids were gently held together for 1–2 seconds. The right eyes were used as the controls. The test and control eyes were examined at approximately 1 hour and 1, 2 and 3 days after application. Grades of ocular reaction were recorded using the Draize scale. If signs of irritation were observed on day 3, the observation period was extended to days 4 and 7 and at least weekly thereafter up to day 21 or until the eyes appeared normal, whichever occurred sooner.

Skin Irritation

Skin irritation was measured by a guinea pig flank test as follows:

Tests were conducted on a group of 6 female guinea pigs weighing 250–350 g. An area approximately 6 cm×5 cm on each flank was clipped. A volume of 100 $\mu$l of the test substance was applied to one flank of each animal and a control (vehicle only or formulation blank) to the other. Approximately 15 minutes after application each guinea pig was observed for 5 minutes and the number of times the animal attempts to reach either flank at the site of application with a full turn of its head recorded. The observations were repeated for 5 minutes at approximately 30 minutes, 1, 2, 3, 4, 5 and 6 hours after application. Observations were done using a video camera with a timing device set to record at the above times. Responses were calculated as the difference in the number of head turns between the test and control flanks. Potential paraesthetic response was qualified according to the following guidelines:

| Mean No. head turns/time point | Classification |
|---|---|
| <5 | practically no response |
| 5–12 | low |
| 13–20 | moderate |
| 21–39 | high |
| >40 | very high |

The results of the toxicological evaluations are shown in Table I.

TABLE I

| Composition | Eye Irritation | Skin Irritation |
|---|---|---|
| EC (dilute) | Moderate/severe (none) | Severe (practically none) |
| Example 2 | — | mild |
| Example 3 | None/moderate | mild |
| SR | Moderate | mild |

The foregoing results show that on the one hand the microencapsulated compositions of this invention possess comparable biological efficacy to non-encapsulated compositions containing the same active ingredient. These results indicate that, though encapsulated, the compositions provide relatively quick release and availability of the active ingredient. On the other hand, the properties regarding eye and skin irritation do not resemble the non-encapsulated products. This combination of properties is and was surprising.

What is claimed is:

1. A process for preparing quick release polyurea microcapsules containing an agriculturally active material comprising the steps of
    (a) preparing an organic phase comprising a water-immiscible material to be encapsulated, an aromatic diisocyanate and optionally an aromatic polyisocyanate containing 3 or more isocyanate groups, wherein when the organic phase comprises the aromatic diisocyanate and the aromatic polyisocyanate, the weight ratio of said polyisocyanate to said diisocyanate is from about 1:50 to about 1:10;
    (b) introducing the organic phase into an aqueous phase comprising water, a protective colloid, and, optionally, a surfactant to form a dispersion of the organic phase in the aqueous phase;
    (c) mixing the dispersion under high shear to form an oil-in-water emulsion in which the oil droplets have an average size of from about 1 to about 5 microns; and
    (d) adjusting as necessary temperature and/or pH of the oil-in-water emulsion such that a polymerization reaction occurs forming the microcapsules containing the organic phase.

2. A process according to claim 1 wherein the organic phase does not contain an aromatic polyisocyanate having 3 or more isocyanate groups.

3. A process according to claim 1 wherein the organic phase comprises an aromatic diisocyanate and an aromatic polyisocyanate having 3 or more isocyanate groups.

4. A process according to claim 1 in which the oil droplets have an average size of from about 2 to about 4.5 microns.

5. A process according to claim 1 in which the aromatic diisocyanate is tolylene diisocyanate.

6. A process according to claim 3 in which the aromatic diisocyanate is tolylene diisocyanate.

7. A process according to claim 1 in which the aromatic polyisocyanate is polymethylene polyphenylisocyanate.

8. A process according to claim 1 in which the material encapsulated comprises a pyrethroid insecticide.

9. A process according to claim 1 in which the material encapsulated comprises lambda-cyhalothrin.

10. A process according to claim 1 in which the material encapsulated comprises fluazifop-P-butyl.

11. Microcapsules produced by the process of claim 1.

12. Microcapsules produced by the process of claim 3.

13. Microcapsules produced by the process of claim 7.

* * * * *